United States Patent
Stocks et al.

(10) Patent No.: US 8,980,631 B2
(45) Date of Patent: Mar. 17, 2015

(54) HIGH-THROUGHPUT CULTURE AND TRANSFER DEVICE AND METHOD

(75) Inventors: Blair Taylor Stocks, Reston, VA (US); Shayn Peirce Cottler, Charlottesville, VA (US); Adam J. Katz, Gainesville, FL (US)

(73) Assignee: University of Virginia Patent Foundation, Charlottesville, VA (US)

( * ) Notice: Subject to any disclaimer, the term of this patent is extended or adjusted under 35 U.S.C. 154(b) by 158 days.

(21) Appl. No.: 13/381,772

(22) PCT Filed: Jun. 30, 2010

(86) PCT No.: PCT/US2010/040615
§ 371 (c)(1),
(2), (4) Date: Apr. 4, 2012

(87) PCT Pub. No.: WO2011/002894
PCT Pub. Date: Jan. 6, 2011

(65) Prior Publication Data
US 2012/0183510 A1    Jul. 19, 2012

Related U.S. Application Data

(60) Provisional application No. 61/221,577, filed on Jun. 30, 2009.

(51) Int. Cl.
*C12N 5/02* (2006.01)
*C12M 1/12* (2006.01)
*C12M 1/32* (2006.01)

(52) U.S. Cl.
CPC ............... *C12M 25/00* (2013.01); *C12M 23/12* (2013.01)
USPC ........................................................ 435/383

(58) Field of Classification Search
None
See application file for complete search history.

(56) References Cited

U.S. PATENT DOCUMENTS

| | | | |
|---|---|---|---|
| 4,304,865 A | 12/1981 | O'Brien et al. | |
| 6,429,008 B1 | 8/2002 | Copeland et al. | |
| 2003/0235519 A1 | 12/2003 | Sha et al. | |
| 2004/0018507 A1 | 1/2004 | Joos et al. | |
| 2008/0193420 A1 | 8/2008 | Kruse et al. | |
| 2010/0086919 A1* | 4/2010 | McKeon | 435/6 |
| 2011/0306122 A1* | 12/2011 | Moritz et al. | 435/325 |

OTHER PUBLICATIONS

International Application Serial No. PCT/US2010/040615, Search Report mailed Aug. 17, 2010, 4 pgs.
International Application Serial No. PCT/US2010/040615, Written Opinion mailed Aug. 17, 2010, 8 pgs.

* cited by examiner

*Primary Examiner* — Allison Fox
*Assistant Examiner* — Yvonne Pyla
(74) *Attorney, Agent, or Firm* — Robert J. Decker; Schwegman Lundberg & Woessner, P.A.

(57) ABSTRACT

A method and device for creating hanging drop cell aggregates. The method and device includes a plurality of pegs that allow for high throughput culture of aggregates. Also disclosed are means of transferring formed aggregates to various destinations, such as well plates, scaffolding, tissues, or wounds. Use of the device permits aggregates to be prepared or created in larger quantities than current methods, and allows for them to be transferred more efficiently.

15 Claims, 12 Drawing Sheets

HIGH-THROUGHPUT CULTURE AND TRANSFER DEVICE AND METHOD

RELATED APPLICATIONS

The present application is a U.S. National Stage Filing under 35 U.S.C. §371 from International Patent Application Serial No. PCT/US2010/040615, filed Jun. 30, 2010, and published on as WO 2011/002894A1 on Jan. 6, 2011, which claims priority from U.S. Provisional Application Ser. No. 61/221,577, filed Jun. 30, 2009, entitled "High-Throughput HASCA Culture and Transfer Plate and Related Method thereof;" each of which is hereby incorporated by reference herein in its entirety.

FIELD OF THE INVENTION

The present invention relates generally to the field of methods and devices used to culture cells. More specifically, the invention is in the subfield of methods and devices used to culture cell aggregates using the hanging drop method.

BACKGROUND OF THE INVENTION

The current method for creating hanging drop cell aggregates is to pipette individual cells onto a slide or a petri dish and invert the cells so that the force of gravity causes the cells to form into aggregates. Once the aggregates have formed, they typically then have to be pipetted again to transfer them to a storage destination, and then again to their ultimate destination for research, treatment, or some other purpose. Generally, this is a slow and inaccurate process, but, until recently, uses of cell aggregates have not required production in quantities large enough to merit improvements on this process. Recent discoveries, however, have led to the need for high-throughput solutions for the cell aggregate formation process.

Another current method involves forming the cell aggregates directly in the specially coated low-attachment well plates or in well plates pre-loaded with a special-purpose scaffolding for forming cell aggregates. A problem with these designs is that the cell aggregates form directly in well plates, and in order to be used, the cell aggregates still must be transferred manually to their next location (e.g. into tissue or into another cell culture chamber) in the time-intensive manner described above.

A further disadvantage is that these methods do not employ the hanging drop method to create cell aggregates. There may be circumstances in which the creating cell aggregates via the hanging drop method (i.e., under the force of gravity) is superior to the methods described above.

SUMMARY OF THE INVENTION

Accordingly, an aspect of an embodiment of the present invention provides a high-throughput means of creating hanging drop cell aggregates. An aspect of an embodiment of the present invention features a culture plate that provides a plurality of pegs to which individual cells can be applied. Under the force of gravity, the cells form cell aggregates. According to various embodiments, the cell aggregates can be transferred to various destinations, including, among others, well plates, scaffoldings and wounds.

An aspect of various embodiments of the present invention may provide a number of advantages. One advantage is that it significantly reduces time for cell aggregate creation and transfer, which will ultimately streamline the use of those aggregates for treatment, research, or other functions. It also increases the percent of aggregates successfully transferred to their destinations and more tightly controls and regulates the ratio total number of aggregates transferred to destination site. It can be manufactured cheaply via polystyrene molding or another similar manufacturing process, which allows it to be disposable to save on sterilization costs and avoid contamination.

An aspect of an embodiment of the present invention provides a method to create cell aggregates. The method may comprise: applying cells to a plurality of pegs of predetermined size (as desired or required) and arranged in a predetermined configuration (as desired or required); and hanging said applied cells from said plurality of pegs to create the cell aggregates.

An aspect of an embodiment of the present invention provides a system/device for creating cell aggregates. The system/device may comprise: a plurality of pegs of predetermined size (as desired or required) and arranged in a predetermined configuration (as desired or required); and said plurality of the pegs themselves are configured for hanging said applied cells from said plurality of pegs to provide the creation of the cell aggregates. The pegs, for example, may be any, protrusion, stud, post, surface area, pedestal, pin, tab, tongue, head, protuberance, etc. An aspect of the configuration of the pegs is such that it allows cells to adhere to the pegs, and as they hang from the pegs, the force of gravity causes the cells to form into aggregates. An aspect of the configuration of the pegs is such that it provides a surface area for the cell aggregates to be created.

An aspect of an embodiment of the present invention provides a method and device for creating hanging drop cell aggregates. The method and device includes a plurality of pegs that allow for high throughput culture of aggregates. Also disclosed are means of transferring formed aggregates to various destinations, such as well plates, scaffolding, tissues, or wounds. Use of the device permits aggregates to be prepared or created in larger quantities than current methods, and allows for them to be transferred more efficiently.

These and other objects, along with advantages and features of the invention disclosed herein, will be made more apparent from the descriptions, drawings, and claims that follow.

SUMMARY OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIG. 4 is a cross section schematic view of a peg that contains a channel to allow forced air or other medium through.

FIG. 5 is a cross section schematic view of a peg that contains a plunger mechanism or the like.

FIG. 11 shows examples of the culture process.

DETAILED DESCRIPTION OF THE INVENTION

Figure 1:
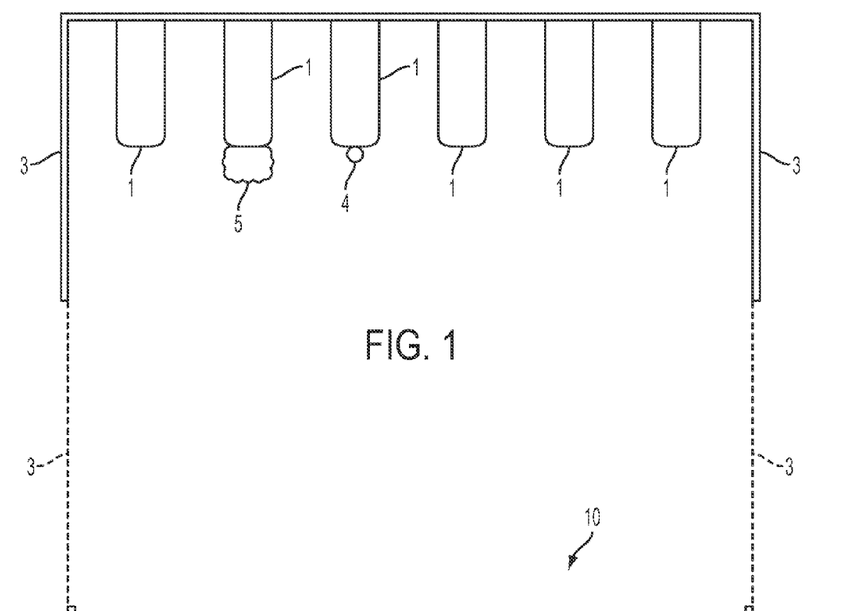
FIG. 1 is a side schematic view of the culture plate containing the pegs on which the aggregates are formed.

Turning now to the drawings, for instance FIG. 1, an aspect of an embodiment of the subject invention may include a culture plate 2 that contains a plurality of pegs 1. The pegs 1 can be varied in diameter according to the desired number of cells in the resulting aggregate. The number, size, configuration, and layout of the pegs can also be varied as needed. The number, size, configuration and layout may be varied for efficient and effective cell aggregate creation, throughput, and transfer. The number, size, configuration and layout of the pegs may vary for compatibility, fit, communication, and interaction with the various components and subcomponents of the various embodiments discussed throughout this disclosure. The number, size, configuration and layout of the pegs may vary to increases the amount or number of cell aggregates created. The number, size, configuration and layout of the pegs may vary to increases the percent, number and volume of aggregates successfully transferred to their destinations. Cells 4 are applied to the pegs 1. The cells 4 adhere to the pegs 1, and as they hang from the pegs, the force of gravity causes the cells to form into aggregates 5.

Figure 2A:
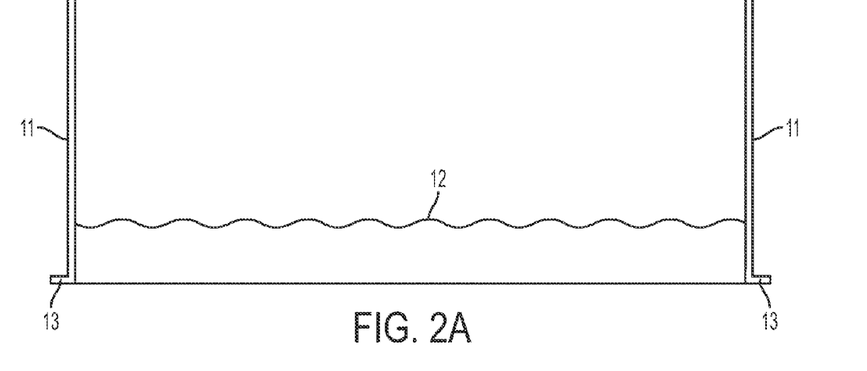
FIG. 2(A) is a side schematic view of the incubation chamber.
Figure 2B:
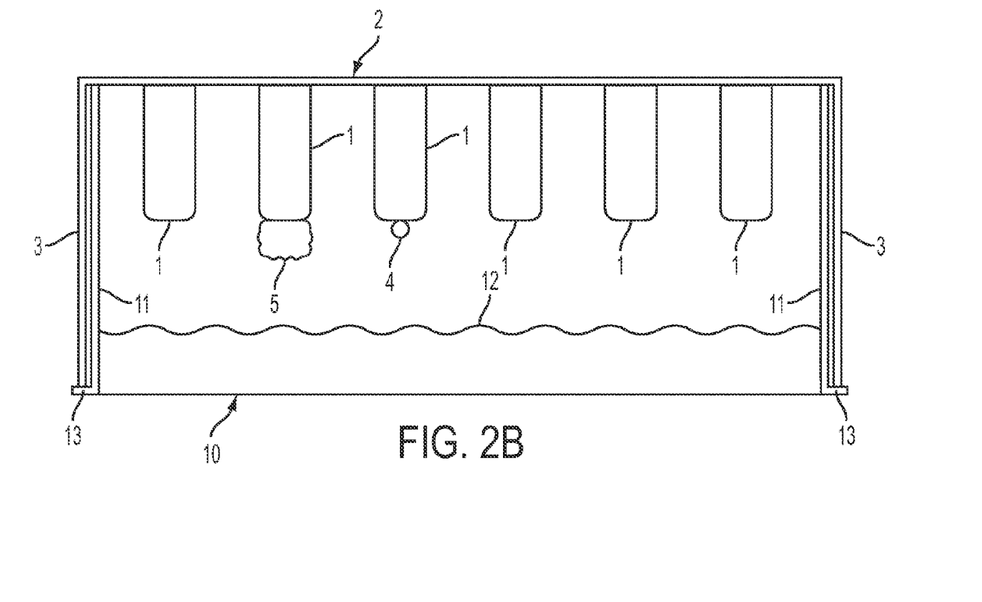
FIG. 2(B) is a side schematic view of the culture plate that is disposed in communication with the incubation chamber.

In an embodiment of the invention, the cells may be incubated for at least some of the time that it takes for the aggregates to form. One way to accomplish the incubation is through use of an incubation chamber 10, as shown in FIG. 2(A). The incubation chamber 10 may be sized to correspond with the culture plate 2, so that the culture plate 2 can rest on the incubation chamber 10 to create a closed chamber, as shown in FIG. 2(B). The walls 11 and protruding edges 13 of the incubation chamber 10 and the walls 3 of the culture plate 2 may be configured to allow the culture plate 2 and incubation chamber 10 to fit snugly together (but not necessarily).

It should be appreciated that the fit or alignment between the culture plate and incubation chamber (as well as any of the components discussed throughout this disclosure) may be accomplished by a variety of interfaces, fit-arrangements, or assemblies. The various components may have complimentary shapes or contours to accommodate one another for interfacing, stacking, communicating or fitting. The components may be fitted using a variety of approaches, such as, but not limited thereto, snap-fit, lock-fit, friction-fit, press-fit, tongue-and-groove fit, etc.

The incubation chamber 10 can be filled with an incubation medium 12. The incubation medium 12 can be phosphate buffer solution, any commercially available medium, or a custom prepared medium. The sides 11 of the incubation chamber 10 may be tall enough to allow cells 4 to hang from the pegs 1 without coming into contact with the incubation medium 12, as shown for instance in FIG. 2(B). While only a single cell 4 and single cell aggregate 5 is shown for the sake of simplicity of illustration, it should be appreciated that a plurality of pegs 1 shall contain the cells 4 and aggregates 5.

An embodiment of the invention may involve applying cells 4 to the pegs 1 while the culture plate 2 rests on a flat surface and the pegs face upwards. The culture plate 2 can then be inverted to accomplish the hanging necessary to form the cell aggregates 5.

Figure 3A:
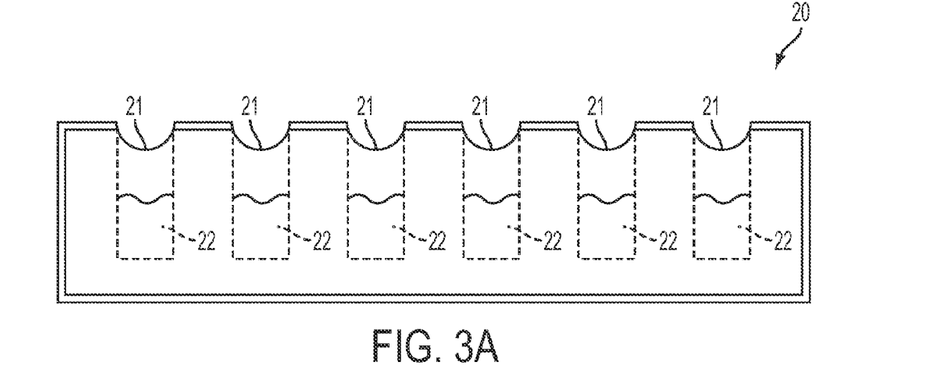
FIG. 3(A) is a side schematic view of a well plate.
Figure 3B:
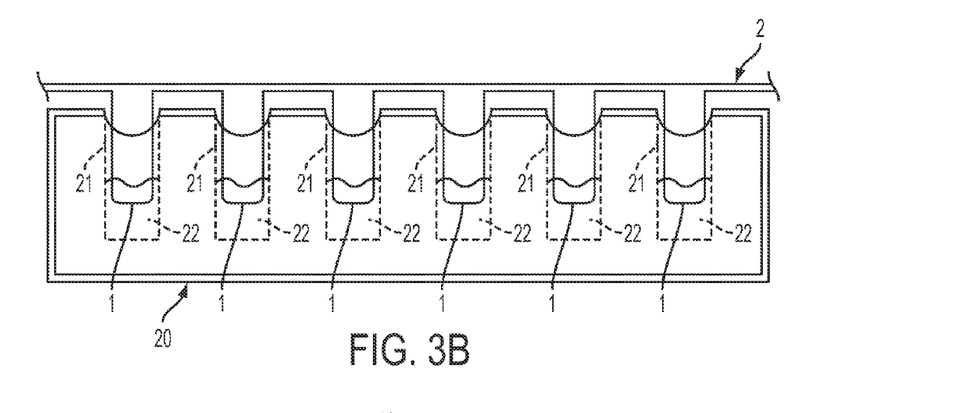
FIG. 3(B) is a side schematic view of a portion of the culture plate that is disposed in the well plate whereby the pegs are at least partially submerged in the medium of the wells.

An aspect of an embodiment of the invention may consist of a well plate 20, as provided in FIG. 3(A). An aspect of an embodiment may comprise transferring the formed cell aggregates 5 to a well plate 20. The well plate 20 may have a number of wells 21 that corresponds to the number of pegs 1 in the culture plate. As shown in FIG. 3(B), the wells 21 may be sized and arranged so that when the culture plate 2 is inverted over the well plate 20, each peg 1 can be inserted into a well 21, at which point the cell aggregates 5 are transferred to the well plate 20. The transferred aggregates can then be used for further culture, maintenance, study, research, characterization, or some other purpose.

One method of transferring the cell aggregates is to fill the wells 21 with a medium 22, as shown in FIG. 3(A). When the cell aggregates come into contact with the medium 22, as shown in FIG. 3(B), they detach from the pegs 1 and fall into the wells 21. The medium may be growth medium or any other desired medium.

Figure 4:
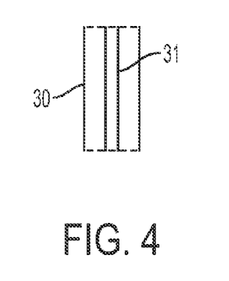

A method of transferring the cell aggregates 5 may be to use air pressure to dislodge the aggregates from the pegs. FIG. 4 shows the cross-section of a peg 30 that contains an air channel 31 that can be used to guide forced air (or other medium, gas, or fluid) so that it comes into contact with the aggregates, although the air could also be directed around the pegs or in some other fashion.

Figure 5:
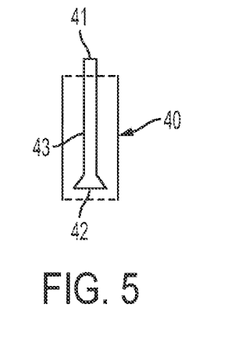

A method of transferring the cell aggregates may be by the application of mechanical force. FIG. 5 shows a cross-section of a peg 40 that contains a mechanical plunger 43. The plunger may be longer than the height of the peg so that a section 41 of it extends above the peg 40 (but not necessarily). During the formation of the cell aggregates, the plunger head 42 may sit above the surface of the peg 40. When transfer to another location is desired, the plunger can be extended, either manually or by a lever, by another mechanical device, or by an electronically or pneumatically controlled device, thus pushing the cell aggregates off of the pegs 40 and into their destination. It should be appreciated that the plunger 43 may be any means for pushing the aggregate from the peg. The push can be any of a variety of contacts, forces, strikes, taps, or collisions. It should be appreciated that the plunger 43 may be an elongated member, extension, stud, contact member, pin, post, protrusion, finger, surface, or some other instrumentality necessary to accomplish the transfer or dislodgement.

A method of transferring the cell aggregates may be by agitating the culture plate 2 with sufficient force to dislodge the cell aggregates. The agitation may be any movement, motion, vibration or shaking necessary to accomplish the dislodgement or transfer. The agitation may be provided mechanically, electrically, electro-mechanically, or manually.

Figure 6A:
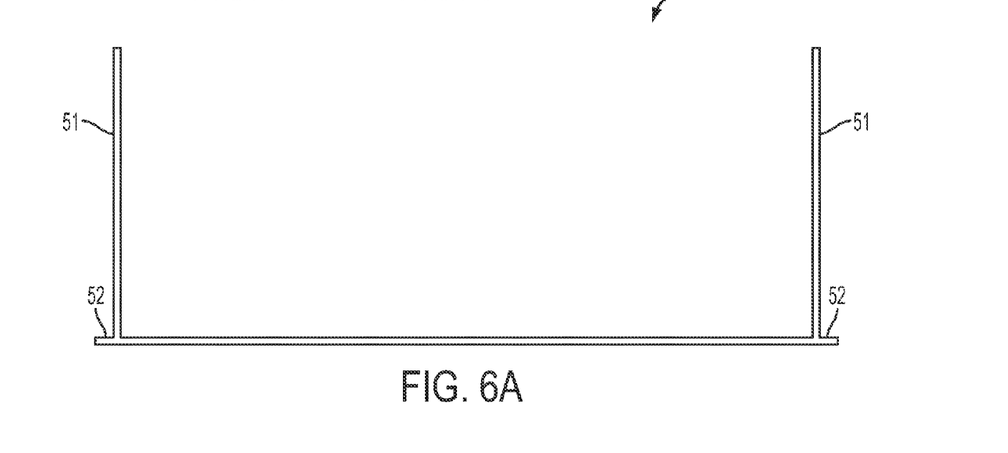
FIG. 6(A) is a side schematic view of the guide plate.
Figure 6B:
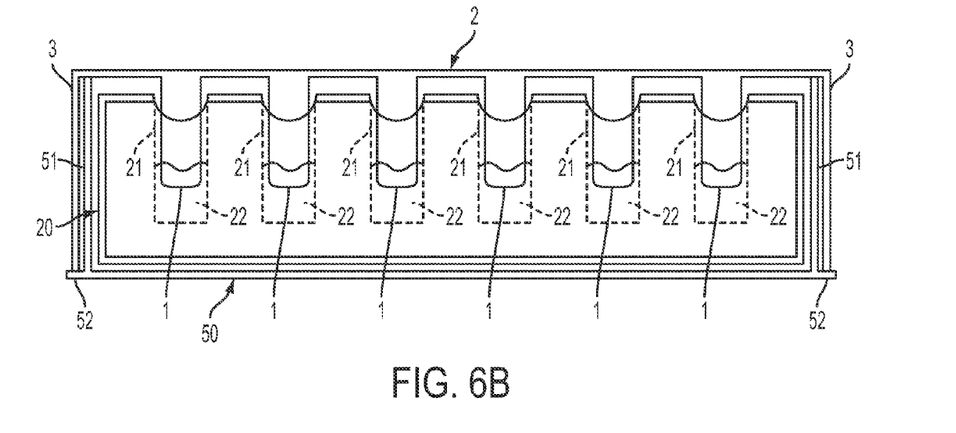
FIG. 6(B) is a side schematic view of the culture plate and well plate aligned within or in communication with the guide plate.

The transfer of cells to a well plate can be further facilitated by using a guide plate 50, as shown in FIG. 6(A), for example. Referring to FIG. 6(A), the guide plate 50 may be sized so that the well plate 20 can be placed inside the guide plate 50 such that the well plate 20 is firmly held in the appropriate position that it will line its wells 21 up with their corresponding pegs 1 in the culture plate 2. The guide plate 50 may be further sized to correspond with the culture plate 2, so that the culture plate 2 can rest on the guide plate 50. The walls 51 and protruding edges 52 of the guide plate 50 and the walls 3 of the culture plate 2 allow the culture plate 2 and guide plate 50 to fit snugly together (but not necessarily). The sides 51 of the guide plate 50 may be of the appropriate height to allow cells to hang from the pegs 1 at a level that is within the corresponding well 21, but not so low that the cell aggregates are crushed or damaged by the bottom of the well 21.

Figure 7:
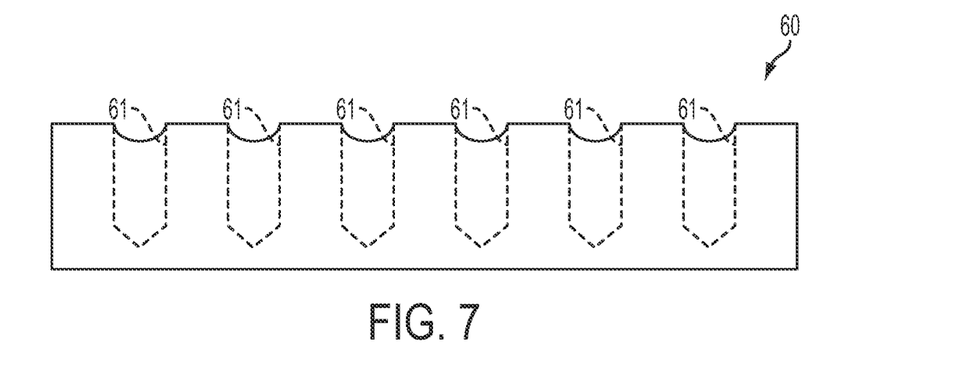
FIG. 7 is a side schematic view of a scaffolding previously prepared with apertures; or alternatively, a view of the scaffolding after it has been prepared wherein the preparation to create the scaffolding is part of an embodiment of the present invention.

An aspect of an embodiment of the invention may include transferring the cell aggregates to a scaffolding 60. FIG. 7 shows a scaffolding 60 that contains apertures 61 that may be spaced and sized to correspond with the location of the pegs 1 on the applicable culture plate 2. The cell aggregates can then be transferred from the culture plate 2 to the scaffolding 60 by positioning the pegs 1 over the corresponding apertures 61 in the scaffolding 60. The transfer can be accomplished using any of the methods of transfer discussed above, throughout this disclosure, or using another method.

It should be appreciated that the apertures 61 can be any of holes, target sites, indentations, pores, a combination thereof, or some other destination site. Furthermore, it should be appreciated that the scaffolding 60 can be any of predetermined destination objects, bandages, sponges, tissue-engineered constructs, biomaterial construct, synthetic, organic, extracellular matrix proteins, synthetic matrix protein, organic matrix protein a combination thereof, or some other destination object.

Figure 8:
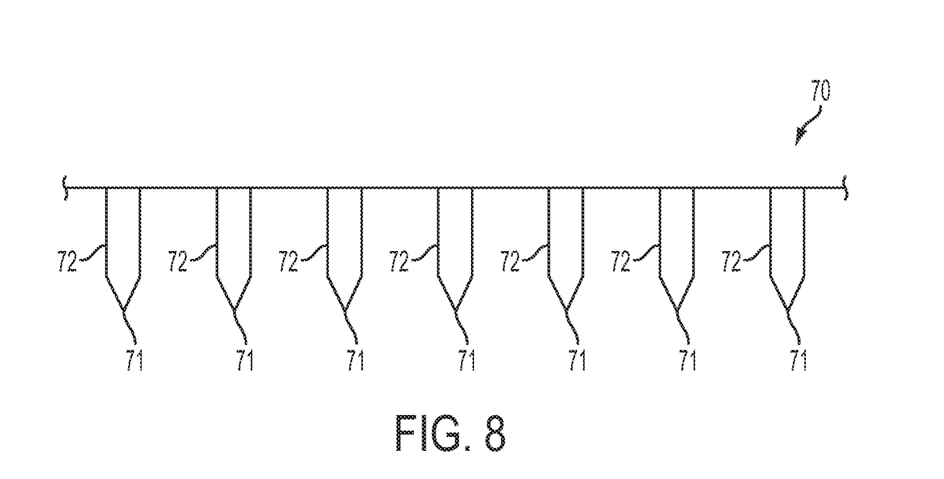
FIG. 8 is a side schematic view of the device used to punch holes in an unprepared scaffolding.

An aspect of an embodiment may include a transfer process that includes preparing an existing scaffolding for transfer. FIG. 8 shows a punch device 70 that can be used to punch holes in an unprepared scaffolding. The punch device 70 contains punch pegs 72 that may be spaced and sized to correspond with the location of the pegs 1 on an applicable culture plate 2. The punch pegs 72 each may have ends 71 that are sharpened to allow them to puncture the scaffolding. Once the scaffolding has been so punctured by the punch device 70, or the like, the transfer process can proceed as discussed above, throughout this disclosure, or using another method.

An aspect of an embodiment of the invention may include a transferring of the aggregates/cells directly to a wound or other tissue bed of a subject. The tissue bed can be any of heart tissue, skeletal muscle tissue, fat tissue, brain tissue, skin, wound, or other tissues.

In various aspects of embodiments of the invention, the cell aggregates can be aggregates of different kinds of cells, including human adipose-derived stromal cell aggregates (HASCA), tumor cell aggregates, mammospheres, stem cell aggregates, or any other cells that form aggregates when hung and subjected to the force of gravity. Furthermore, it is possible to mix more than one cell type to create hybrid aggregates.

EXAMPLES

Practice of an aspect of an embodiment (or embodiments) of the invention will be still more fully understood from the following examples and experimental results, which are presented herein for illustration only and should not be construed as limiting the invention in any way.

Example 1

Prototype

Figure 9A:
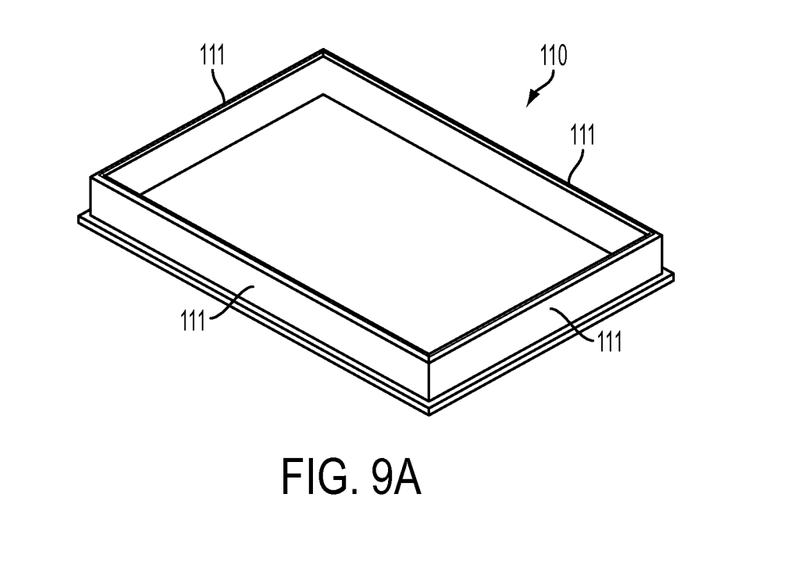
FIGS. 9(A)-(B) show solidworks images of the guide plate and culture plate, respectively.
Figure 9B:
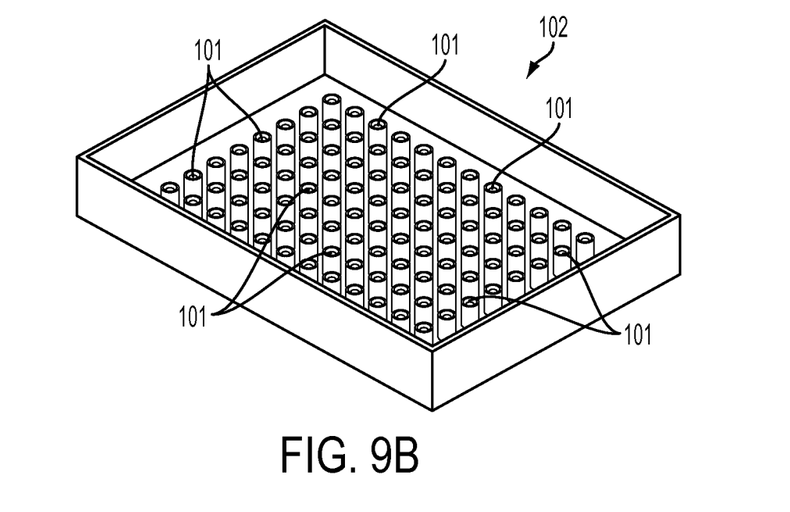
Figure 10A:
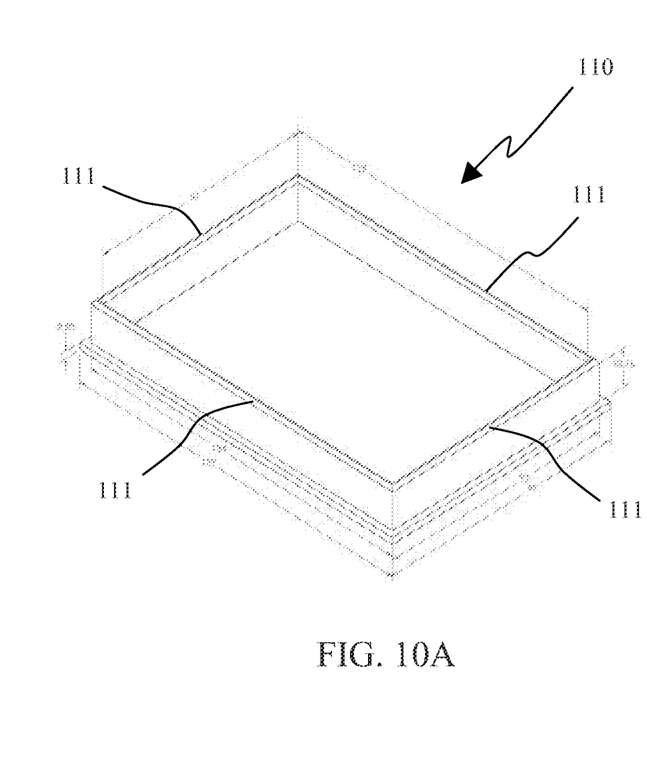
FIGS. 10(A)-(B) show exemplary (non-limiting) dimensions of guide plate and culture plate, respectively. All dimensions are expressed in millimeters.
Figure 10B:
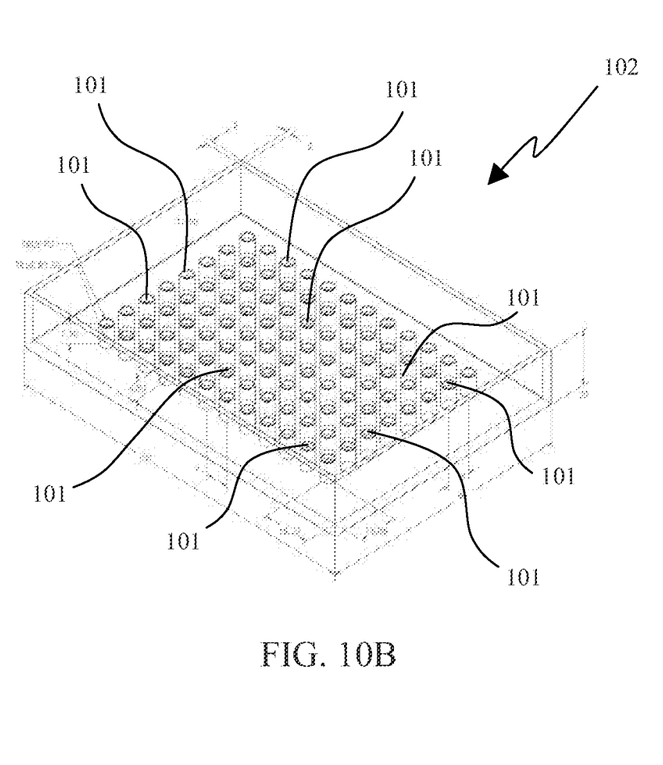

Corning 96 well flat bottom plate was used as a guideline for exemplary dimensions of a prototype. Using Solidworks drafting software, a bottom plate 110 (See FIGS. 9(A) and 10(A)) was designed to house a 96-well well plate 120 (the well plate being shown in FIG. 11(C)) during human adipose-derived stromal cell aggregate (HASCA) transfer. The bottom plate 110 may also as act as an incubation chamber, for example, a hydration chamber during culture. A culture plate 102 (See FIGS. 9(B) and 10(B)) was designed to fit around the lip 111 of the bottom plate 110 (e.g., base plate or incubation chamber) and over the 96-well well plate 120 when inverted. The 96-well well plate 120 has 96 five mm diameter pegs 101, being 7.5 mm tall and arranged in an 8×12 array negative to the wells 121 of the 96-well well plate 120 and acts as hanging drop HASCA culture locales. Dimensions of the device are given for reproducibility and are not intended to be limiting, See FIGS. 10(A)-(B)). Using a Dimension SHDM1000 (Stratasys, Inc) Rapid Prototyping machine, the SolidWorks files were converted to STL file types and both bottom plates were printed with ABS Plastic.

Figure 11A:
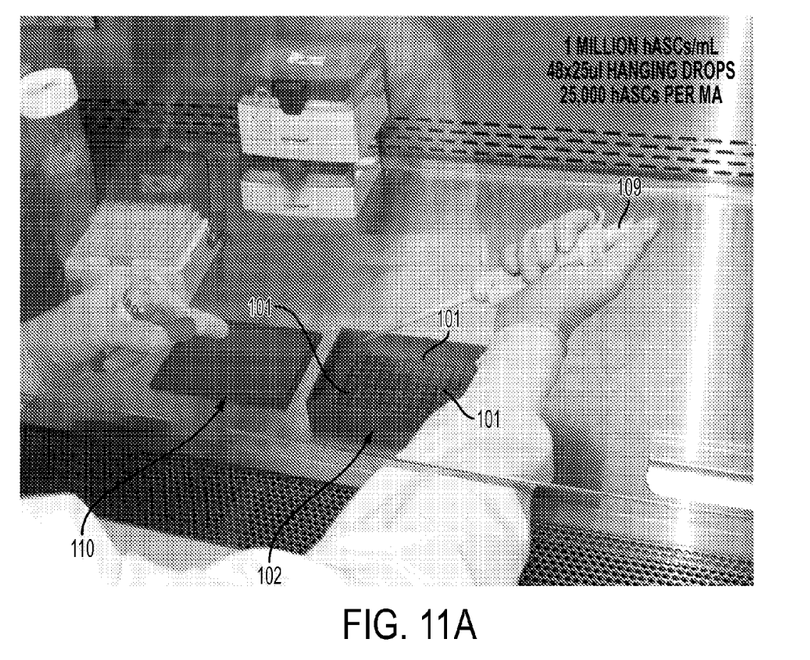
FIG. 11(A) illustrates pipetting 48 25 uL hanging drop cultures (25000 hASCs per drop) on culture plate pegs.
Figures 11B, 11E:
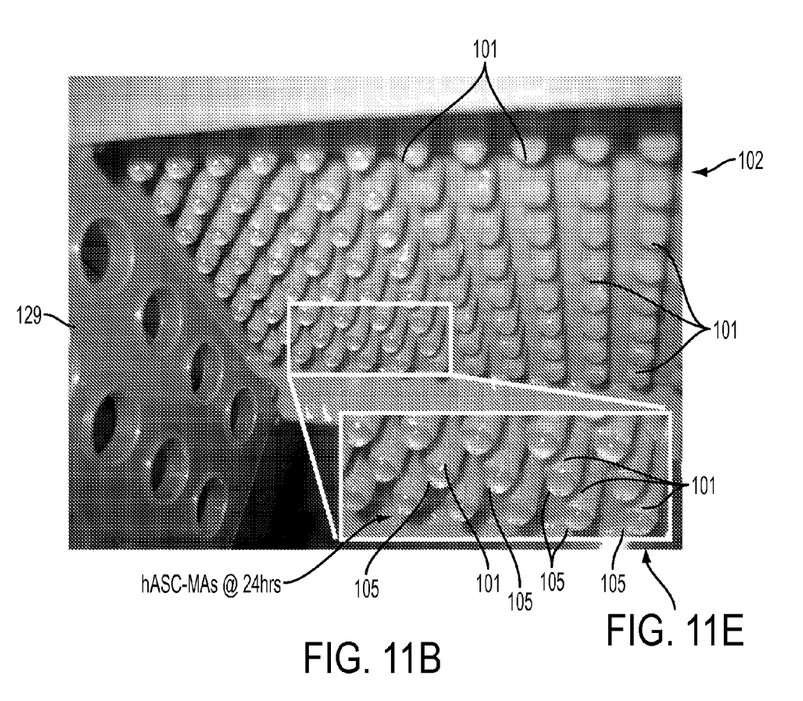
FIG. 11(B) illustrates HASCA formation after incubation for 24 hours.
FIG. 11(E) provides an enlarged portion of the culture plate and pegs as illustrated in FIG. 11(B).

To culture HASCAs, the culture plate 102 and incubation plate 110 are first sterilized using an ethanol/UV treatment for fifteen minutes. A multichannel pipette would pipette eight 25 uL cultures (at 25,000 HASCs per drop) at a time on each of the pegs 101. The bottom plate 110 (e.g., incubation chamber) would be filled with sterile PBS to act as an incubation or hydration chamber. The culture plate 102 would then be inverted, set atop the bottom plate 110 (e.g., incubation chamber), and incubated at 37 degrees Celsius at 5% $CO_2$ for 24 hours to form HASCAs in hanging drop cultures 105 (See FIGS. 11(B) and 11(E)). After 24 hours, the culture plate 102 would be removed from the base plate 110 and the PBS can be drawn out of the bottom plate 110 (e.g., incubation chamber).

Figure 11C:
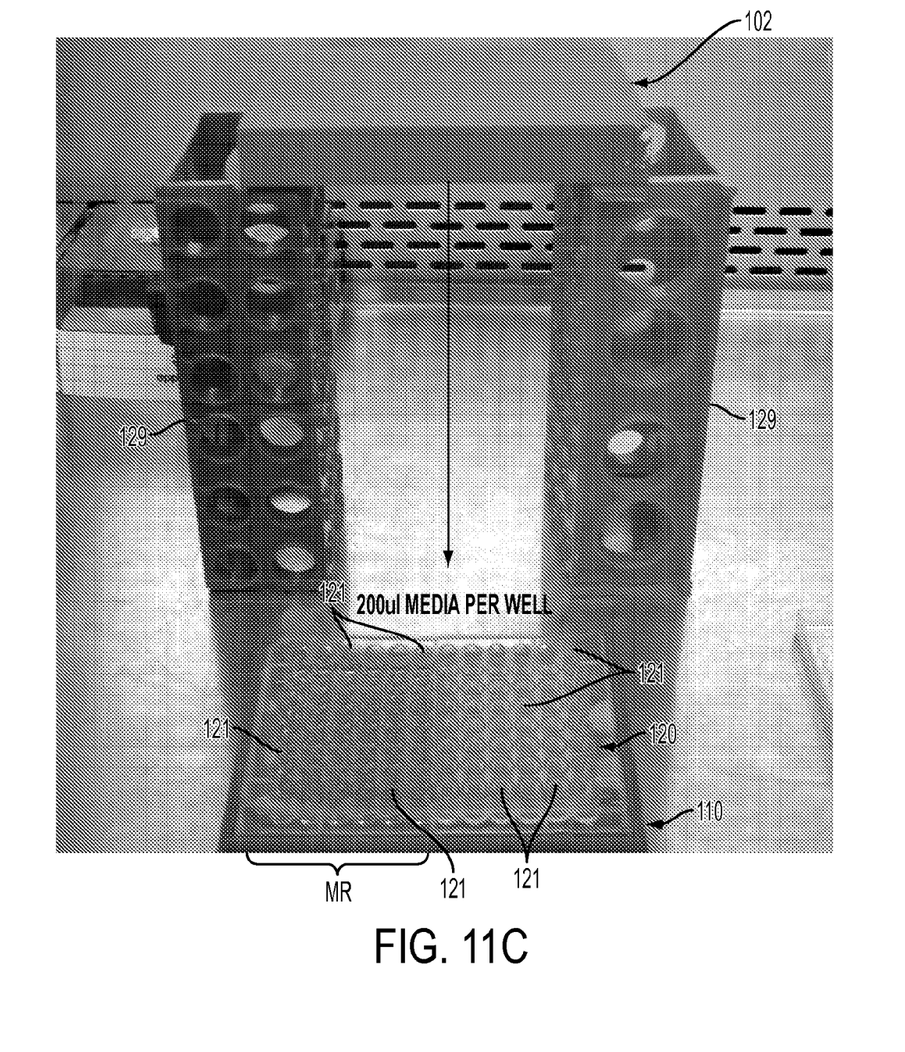
FIG. 11(C) illustrates guide plate with 96 well plate filled with 200 uL of media.

Next, a sterile 96 well plate 120 would be placed in the bottom plate 120, which now acts as a guide plate, and then each well 121 (See FIG. 11(C)) is filled with 200 uL of 1% HS-LADPM media (HASC proprietary, Adam Katz). The inverted culture plate 102 would then be placed over the 96-well well plate 120 forcing the hanging drop HASCA cultures 105 to come in contact with the media (generally illustrated as darker region in FIG. 11(C), and designated by region labeled "MR") in the wells 121. Upon contact, the force of gravity would cause the HASCAs 105 to drop into the 96-well well plate 120. HASCAs 105 in the 96-well well plate 120 could then be stored up to a month, for example, until chronic wound treatment.

Example 2

Experiment and Result Set

The following experiment was carried out to compare the current method of HASCA culture and transfer (pipetting hanging drop cultures on the inside lids of petri dishes and transferring HASCAs individually to an ultra low attachment plate with a single channel pipette) to the culture and transfer of HASCAs using a specific embodiment of the present invention.

Method (Control)

Figure 12A:
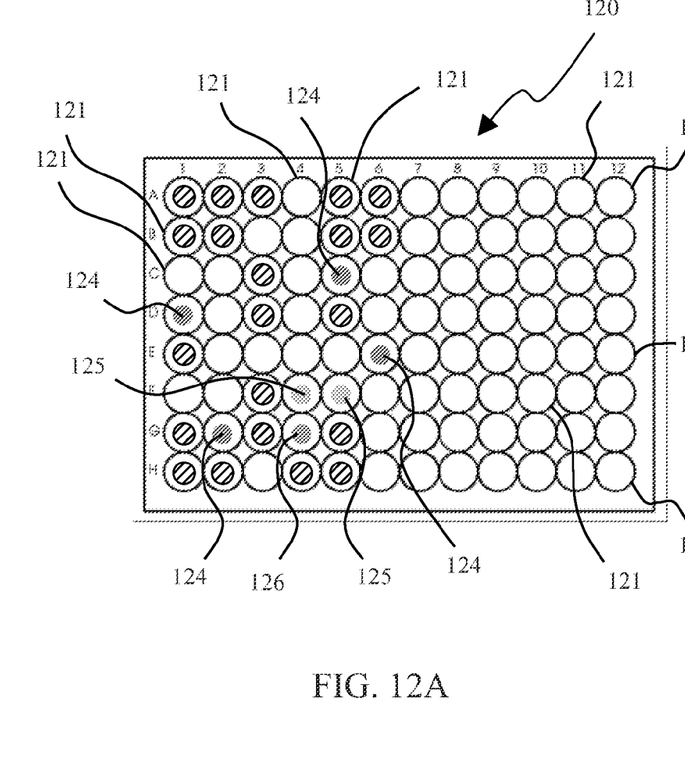
FIG. 12 is a schematic of HASCAs transferred to 96 well plate (having a flat bottom) via individual pipette (FIG. 12(A)) versus a prototype of a specific embodiment of the present invention (FIG. 12(B)). The slash-mark shaded circle inset in the wells correspond to 1 HASCA per well. Insets labeled 124 in the wells correspond to two HASCA per well. Insets 125 in the wells correspond to three HASCA per well. The inset labeled 126 in the wells correspond to four HASCA per well.

Passage 3 HASCs from donor h8-07 (Katz Lab, UVa Health System) were grown to confluence in 8 t75 dishes in DMEM F-12 10% calf serum media. Cells were lifted using TryPLE, counted with a hemacytometer, then resuspended at a concentration of 1 million HASCs per mL. Using a single channel pipette 48 25 uL drops (25,000 HASCs each) were pipetted on the inside lids of 6 petri dishes. The bases of petri dishes were filled halfway with sterile PBS, the lids inverted and then placed over the dish bases. Dishes were incubated at 37 degrees Celsius at 5% CO2 for 24 hours. Petri dishes were imaged under a stereomicroscope at 100× and the total number of HASCAs cultured was counted (Table 1). Petri dish lids were then removed and re-inverted in a laminar flow hood. A single channel pipette was then used to lift HASCAs individually from the inside lids and into an ultra low attachment plate with wells filled with 200 uL of DMEM F-12 10% calf serum media. The time to transfer all HASCAs was recorded (See Table 1). The 48 wells filled with media were imaged with an inverted microscope at 100×. ImageJ was used to determine the average diameter of ten HASCs (Table 1). A schematic of HASCAs transferred to the 96-well well plate 120 was diagrammed to determine the percent of HASCAs transferred and the ratio of HASCAs to well (See FIG. 12(A)). The slash-mark circle insets in the wells 121 correspond to 1 HASCA per well. The inset identified as 124 in the wells 121 correspond to two HASCAs per well. The insets identified as 125 in the wells 121 correspond to three HASCAs per well. The inset identified as 126 in the wells 121 correspond to four HASCAs per well. As shown in FIG. 12(A), 39 of 48 wells received HASCA, while 9 of the 48 did not transfer at all.

Method (Prototype)

Figure 11D:
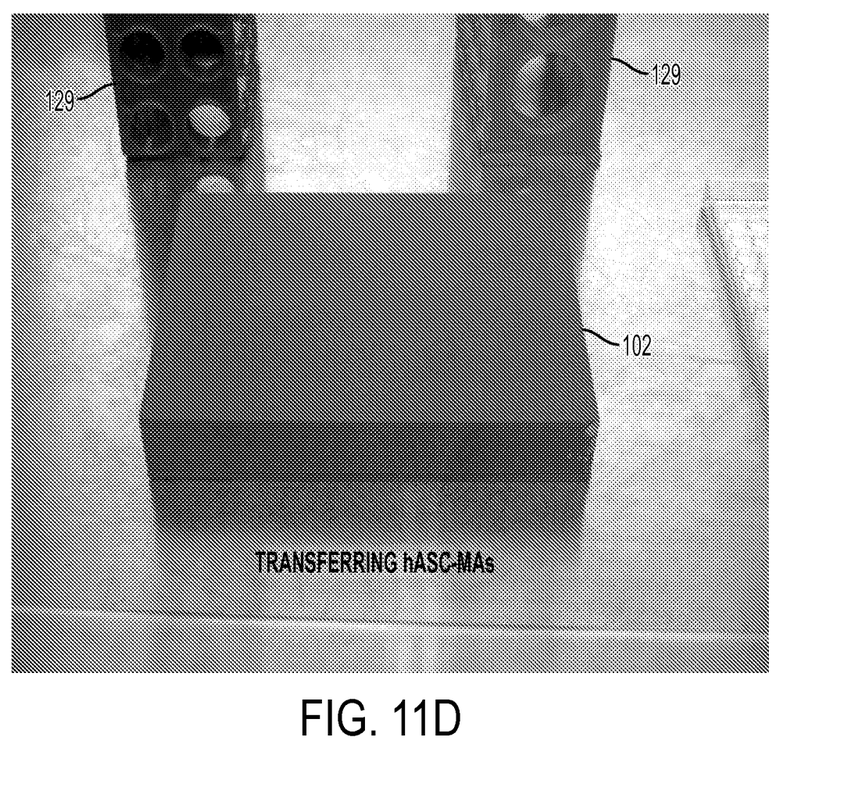
FIG. 11(D) illustrates transferring HASCAs from culture plate to well plate (well plate is obstructed from view by the culture plate).
Figure 12B:
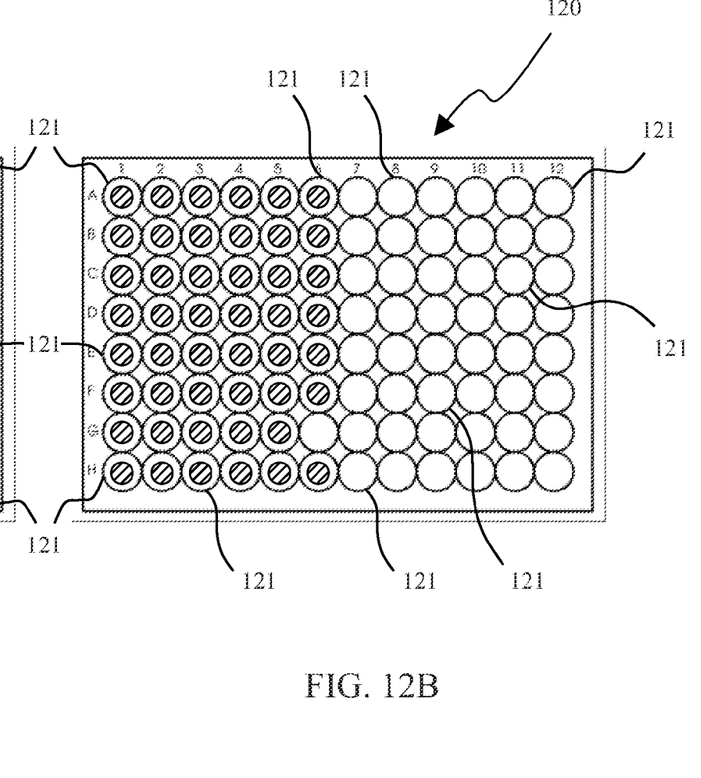

Passage 3 HASCs from donor h8-07 were grown to confluence in 8 t75 dishes in DMEM F-12 10% calf serum media. Cells were lifted using TryPLE, counted with a hemacytometer, then resuspended at a concentration of 1 million HASCs per mL. The prototype was sterilized with ethanol and UV light for fifteen minutes. Using a single channel pipette 109 (although it should be appreciated that a multichannel pipette may be used) 48 25 uL drops (25,000 HASCs each) were pipetted (See FIG. 11(A)) onto half of the pegs 101 in the prototype culture plate 102. The bottom plate 110 (e.g., incubation chamber) 110 was filled with 20 mL of sterile Phosphate Buffer Solution (PBS), the culture plate 102 was inverted, and placed on the bottom 110 plate (e.g., incubation chamber 110), and then incubated at 37 degrees Celsius at 5% $CO_2$ for 24 hours. The cell culture plate 102 was removed from the bottom plate 110, supported by two plastic centrifuge tube holders 129 then imaged from below (i.e., peg side) using a Canon Digital Elph (See FIG. 11(B)). The total number of cultured HASCAs 105 was counted (See Table 1). PBS was then drawn out of the bottom plate 110 and a sterile 96-well well plate 120 was placed in the bottom plate 110 now acting as a guide plate. Half of the wells 121 in the 96-well well plate (i.e., 48 wells) were filled with 200 uL of DMEM F-12 10% calf serum media (See FIG. 11(C)) generally illustrated as darker region in FIG. 11C, and designated by region "MR"). The inverted culture plate 102 was then placed atop the bottom plate 110 (now acting as a guide plate) to transfer HASCAs (See FIG. 11(D)). As illustrated, the culture plate 102 obstructs the view of the bottom plate 110 that is inside or underneath the culture plate. The time it took to transfer HASCAs was recorded (See Table 1). The 48 wells filled with media were imaged with an inverted microscope at 100×. A schematic of HASCAs transferred to the 96-well plate was diagrammed to determine the percent of HASCAs transferred and the ratio of HASCAs to well (See FIG. 12(B)). Still referring to FIG. 12(B), the slash-mark circle insets in the wells 121 correspond to 1 HASCA per well. Also, as shown in FIG. 12(B), 47 of 48 wells received HASCAs.

TABLE 1

Design specification 1 and 2 metrics for control and experimental HASCA culture and transfer.

|  | Petri Dish Culture and Individual Pipette Transfer (Control) | Prototype (Experimental) |
|---|---|---|
| Size of HASCA Cultured | 277.5 um +/− 15.8 um | 265.3 +/− 16.7 um |
| Percent HASCAs Cultured | 100% (48/48) | 98% (47/48) |
| Percent HASCAs Transferred (per Diagram 1) | 81% (39/48) | 100% (47/47) |
| Time to Transfer HASCAs | 1 hour | 10 seconds (time to align culture and base plates) |
| Ratio HASCA to Well (per FIG. 12) | Wells ranged from 0:1 to 4:1 | All Wells 1:1 |

The results indicate that this prototype was able to effectively culture nearly the same percentage of HASCAs (98% versus control 100%). Additionally, the prototype outperformed the transfer control method by increasing the percent transfer from 81% to 100%, decreasing the transfer time from 1 hour to 10 seconds, and normalizing the ratio of transferred HASCAs per well from a non uniform range of 0:1 to 4:1 to a uniform 1:1.

The devices, systems, compositions, cells, cell aggregates and methods of various embodiments of the invention disclosed herein may utilize aspects disclosed in the following references, applications, publications and patents and which are hereby incorporated by reference herein in their entirety:

1. Falanga V, Iwamoto S, Chartier M, Yufit T, Butmarc J, Kouttab N, Shrayer D, Carson P. (2007). Autologous bone marrow-derived cultured mesenchymal stem cells delivered in a fibrin spray accelerate healing in murine and human cutaneous wounds. *Tissue Eng* 13 (6): 1299-312.
2. Garcia-Olmo D, Garcia-Arranz M, Herreros D, Pascual I, Peiro C, Rodriguez-Montes J A. (2005). A phase I clinical trial of the treatment of Crohn's fistula by adipose mesenchymal stem cell transplantation. *Dis Colon Rectum* 48 (7): 1416-23.
3. Peirce-Cottler S, Katz A. (2008). FDA Pre-IND Meeting Packet: Autologous Human Adipose Stromal Cells (hASCs) for Healing Diabetic Wounds. UVa Depts. of Biomedical Engineering and Plastic Surgery.
4. http://catalog2.corning.com/lifesciences/media/equipment_compatibility/MD_Microplate_Dimension_Sheets_96_Well.pdf 5. SolidWorks 2008 SP2.1. UVa License. Department of Biomedical Engineering.
6. Lee J C, Kandula S, and Sherber N S. (2009) Beyond Wet-to-Dry: A rational approach to Treating Chronic Wounds. *E-Plasty.* 9:e14.
7. Fonder M A, Lazarus G S, Mamelak A J, et al. Treating the chronic wound: A practical approach to the care of non-healing wounds and wound care dressings. *J Am Acad Dermatol.* 2008; 58(2):185-206.
8. Allenet B, et al. Cost-effectiveness modeling of Dermagraft for the treatment of diabetic foot ulcers in the French context. 2000 April; 26(2):125-32.
9. Fisher Scientific. Corning Ultra-Low Attachment Plates.
10. U.S. Pat. No. 5,858,770, Perlman, "Cell Culture Plate with Oxygen and Carbon Dioxide Permeable Waterproof Sealing Membrane", Jan. 12, 1999.
11. U.S. Design Pat. No. U.S. D469,554 S, Lagond, et al., "Multi-Well Plate", Jan. 28, 2003.
12. U.S. Pat. No. 7,413,910, Kearney, et al., "Multi-Well Apparatus", Aug. 19, 2008.
12. U.S. Patent Application Publication No. U.S. 2007/0269850 A1, Crespi, et al., "Elastomeric Device for Cell Seeding on the Bottom of a Filter", Nov. 22, 2007.
13. U.S. Patent Application Publication No. U.S. 2004/0141895 A1, Sha, "Protein Crystallography Hanging Drop Multiwell Plate", Jul. 22, 2004.
14. U.S. Pat. No. 6,783,732 B2, Madden, et al., "Apparatus and Method for Avoiding Cross-Contamination Due to Pendent Drops of Fluid Hanging From Discharge Conduits", Aug. 31, 2004.
15. U.S. Pat. No. 5,358,871, Stevens, et al., "Culture Vessel", Oct. 25, 1994.

The devices, systems, compositions, cells, cell aggregates and methods of various embodiments of the invention disclosed herein may utilize aspects disclosed in the following references, applications, publications and patents and which are hereby incorporated by reference herein in their entirety:

U.S. patent application Ser. No. 12/444,412 entitled "Methods and Compositions, Useful for Diabetic Wound Healing," filed Jan. 7, 2010;

International Patent Application No. PCT/US2007/021432 entitled "Methods and Compositions Useful for Diabetic Wound Healing," filed Oct. 5, 2007;

U.S. patent application Ser. No. 12/580,417 entitled "Compositions And Methods For Regulating Extracellular Matrix Production In Adipose Derived Cells," filed Oct. 16, 2009;

U.S. patent application Ser. No. 12/580,419 entitled "Compositions and Methods for Modular Soft Tissue Repair," filed Oct. 16, 2009;

International Patent Application No. PCT/US2009/033220 entitled "Spraying Device and Related Method for Cell Aggregates and Cell Aggregate Suspension thereof," filed Feb. 5, 2009;

U.S. patent application Ser. No. 12/162,523 entitled "Methods of Preparing and Characterizing Mesenchymal Stem Cell Aggregates and Uses Thereof," filed Jul. 29, 2008;

International Patent Application No. PCT/US2007/002572 entitled "Methods of Preparing and Characterizing Mesenchymal Stem Cell Aggregates and Uses Thereof," filed Jan. 30, 2007;

U.S. patent application Ser. No. 12/066,348 entitled "Methods and Compositions for Growing Adipose Stem Cells," filed Mar. 19, 2008;

International Patent Application No. PCT/US2006/034915 entitled "Methods and Compositions for Growing Adipose Stem Cells," filed Sep. 8, 2006. (01187-03); and PCT International Application No. PCT/US2007/001896, filed on Jan. 25, 2007 to Laurencin, et al., entitled "Methods for Regulating Gelation of Polysaccharide Solutions and Uses Thereof."

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension, configuration, or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed:

1. A method to create hanging drop cell aggregates, said method comprising:
    applying cells to a plurality of pegs of predetermined size and arranged in a predetermined configuration; and
    hanging said applied cells from said plurality of pegs, wherein said hanging comprises inverting said plurality of pegs, so as to create the hanging drop cell aggregates.

2. The method of claim 1, further comprising:
incubating said applied cells at least a portion of the time while said aggregates are created.

3. The method of claim 2, further comprising:
providing an incubation chamber sized in accordance with said plurality of pegs containing said aggregates; and
inverting said pegs over said incubation chamber during at least a portion of the said incubation duration.

4. The method of claim 3, further comprising:
filling said incubation chamber with an incubation medium.

5. The method of claim 1, further comprising:
providing a well plate, wherein said well plate comprises a plurality of wells that are spaced and sized in accordance with said plurality of said pegs having said aggregates; and
transferring said aggregates from said plurality of pegs to respective said plurality of wells of said well plate by positioning said plurality of pegs to coincide with said plurality of wells.

6. The method of claim 5, wherein:
said plurality of wells contain a medium; and
said transferring of said aggregates comprises contacting said aggregates with said medium.

7. The method of claim 5, wherein:
said transferring of said aggregates comprises applying forced air to said aggregates, pushing said aggregates with sufficient force to dislodge said aggregates or agitating said plurality of pegs with sufficient force to dislodge said aggregates.

8. The method of claim 5, further comprising:
said plurality of pegs is disposed on a culture plate; and
providing a guide plate, wherein said positioning comprises aligning said culture plate with said guide plate.

9. The method of claim 1, further comprising:
providing a scaffolding, said scaffolding comprising a plurality of apertures spaced and sized in accordance with the plurality of said pegs having said aggregates; and
transferring said aggregates from said plurality of pegs to respective said plurality of apertures in said scaffolding by positioning said plurality of pegs to coincide with said plurality of apertures.

10. The method of claim 9, wherein said apertures comprise at least one of: holes, target sites, indententations, pores or any combination thereof.

11. The method of claim 9, wherein said scaffolding comprises at least one of: bandage, sponge, tissue-engineered construct, biomaterial construct, synthetic matrix protein, organic matrix protein, extracellular matrix protein, or a combination thereof.

12. The method of claim 9, wherein:
said transferring of said aggregates comprises applying forced air to said aggregates, pushing said aggregates with sufficient force to dislodge said aggregates or agitating said plurality of pegs with sufficient force to dislodge said aggregates.

13. The method of claim 1, further comprising:
transferring said aggregates from said plurality of pegs to a wound or other tissue bed of a subject.

14. The method of claim 13, wherein the wound or other tissue bed of a subject comprises at least one of: heart tissue, skeletal muscle tissue, fat tissue, brain tissue, skin, or other tissues.

15. The method of claim 1, wherein said aggregates comprise at least one of:
human adipose-derived stromal cell aggregates, tumor cell aggregates, mammospheres, stem cell aggregates, hybrid cell aggregates or any and all cell types and combinations thereof.

* * * * *